United States Patent [19]
Durante et al.

[11] Patent Number: 5,952,532
[45] Date of Patent: Sep. 14, 1999

[54] HYDROXYLATION OF AROMATICS USING MOLECULAR OXYGEN AS THE TERMINAL OXIDANT WITHOUT COREDUCTANT

[75] Inventors: Vincent A. Durante, West Chester; Tilak P. Wijesekera, Glen Mills; Swati Karmakar, Malvern, all of Pa.

[73] Assignee: Sunoco, Inc., Philadelphia, Pa.

[21] Appl. No.: 08/904,168

[22] Filed: Jul. 31, 1997

[51] Int. Cl.[6] .................................................. C07L 37/00
[52] U.S. Cl. ........................................... 568/802; 568/735
[58] Field of Search ...................................... 568/802, 735

[56] References Cited

U.S. PATENT DOCUMENTS

| | | |
|---|---|---|
| 4,982,015 | 1/1991 | Chao et al. . |
| 4,992,600 | 2/1991 | Chao et al. . |
| 5,110,995 | 5/1992 | Kharitinov et al. . |
| 5,233,097 | 8/1993 | Nemeth et al. . |
| 5,861,536 | 1/1999 | Durante .................................. 564/408 |

FOREIGN PATENT DOCUMENTS

| | | |
|---|---|---|
| 02-115138 | 4/1990 | Japan . |
| 03-236338 | 10/1991 | Japan . |
| 07-238042 | 9/1995 | Japan . |

OTHER PUBLICATIONS

U.S. application No. 08/903,983, Durante et al., filed Jul. 31, 1997.

Kitano et. al., Bull. Chem. Soc. Japan. vol., 67, No. 10, pp. 2850–2855, (1994). "Gas phase Oxidation of Benzene to Phenol under the Simultaneous Feeding of Hydrogen and Oxygen. III. Catalyst Prepared from Cu(11) Phosphate".

Jintoku et. al., Chemistry Letters pp. 1687–1688, (1990) Chemistry Letters [The Chemistry Society of Japan] "Palladium Catalyzed Transformation of Benzene to Phenol with Molecular Oxygen".

Miyake et. al., Applied Catalysis A: General vol. 131, pp. 33–42, (1995). "Direct Synthesis of Phenol by Hydroxylation of Benzene with Oxygen and Hydrogen".

de Resende et. al., Preparation of Catalysts V1—Scientific Bases for the Preparation of Heterogeneous Catalysts, pp. 1050–1067, (1995). "Synthesis and Characterization of Titanium Oxide Monolayer".

Kodama et. al., Bull. Chem. Soc. Japan., vol. 68, pp. 1627–1633, (1995). "Formation Equilibrium of a Copper(11)–Binuclear Complex of a New Pyridyl–Containing Tetraoxo Octaaza Macrocyclic Ligand and Its Polarographic Reduction Behavior".

Lam et. al. J. Chem. Soc., Chem. Commun., pp. 2439–2440, (1994). "Synthesis of Novel Dinickel(11) and Nickel(11)–Copper(11) Bimetallic Complex derived from and Acyclic Dinucleating Schiff Base–Pyridine Ligand".

*Primary Examiner*—Michael L. Shippen
*Attorney, Agent, or Firm*—Pepper Hamilton LLP

[57] ABSTRACT

A process is disclosed for the catalytic hydroxylation of aromatic hydrocarbons which comprises contacting aromatic feedstock with oxidant comprising molecular oxygen, under suitable reaction conditions, in the presence of a catalyst comprising three essential components: a support; transition metal selected from the group consisting of vanadium, niobium, copper, palladium, nickel and silver, or combinations thereof, and a promoter comprising a multidentate chelating, binucleating ligand. The catalysts may further comprise additional metal ions. The process is particularly suited, for example, to the one-step conversion of benzene to phenol.

24 Claims, No Drawings

HYDROXYLATION OF AROMATICS USING MOLECULAR OXYGEN AS THE TERMINAL OXIDANT WITHOUT COREDUCTANT

FIELD OF THE INVENTION

This invention pertains to the hydroxylation of aromatic hydrocarbons, for example, the hydroxylation of benzene to phenol, using molecular oxygen as terminal oxidant and to catalysts useful in such processes.

BACKGROUND OF THE INVENTION

Phenol is a valuable commodity intermediate chemical which is among the top 10 organic chemical monomers produced in the US. Principal applications for phenol are as an intermediate to bisphenol A (used in turn to make polycarbonates); as a component in phenol-aldehyde resins, coatings, and adhesives; as a precursor to caprolactam (precursor to Nylon-6), detergents, antioxidants, and to a number of other chemicals which are used in diverse applications. Other hydroxylated aromatics are also of commercial importance. For example, cresols are used largely to manufacture herbicides and insecticides and antioxidants; 2,6-xylenol is the starting material for polyphenylene oxide, a thermoplastic with high heat and chemical resistance and excellent electrical properties developed by General Electric Co. Salicylic acid, dihydroxybenzenes including resorcinol, pyrocatechol, and hydroquinone are also derivatives.

Starting from benzene, the dominant current route to phenol is the "cumene peroxidation process" which requires multiple steps and produces coproduct acetone, markets for which are expected to grow much more slowly than those for phenol. This route also consumes propylene for which there are alternative applications which often produce greater economic return. In this process, benzene is first alkylated to cumene with propylene. Then in a second step, cumene is oxidized with air to the hydroperoxide which, in turn, is subsequently decomposed in the presence of acid to a 1:1 mixture of acetone and phenol:

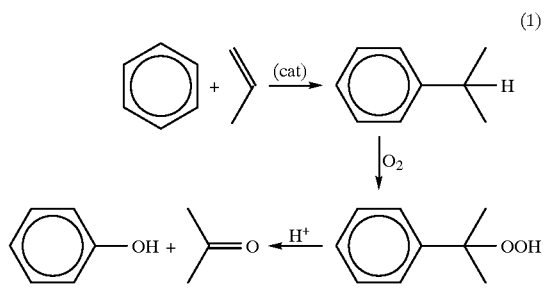

(1)

Another route to phenol which accounts for less than 2% of industrial capacity in the US, is the "toluene oxidation route" In this route, toluene, not benzene, is catalytically oxidized to benzoic acid. In a second step, the benzoic acid is catalytically oxidatively decarboxylated to a 1:1 ratio of phenol and carbon dioxide, the latter being another usually undesired "greenhouse gas" byproduct. In addition to producing a low value byproduct, this route is also capital intensive due to the need for a complex product and catalyst recovery scheme:

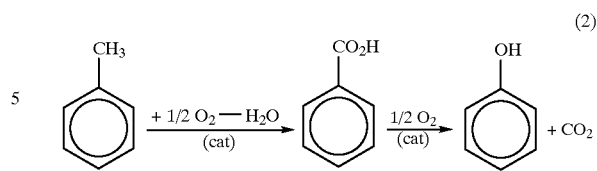

(2)

Still other obsolete routes to phenol through halobenzene intermediates are known in the art, but these are no longer practiced commercially. Cresols and xylenols can be prepared by methylation of phenol with methanol in gas or liquid phase processes.

A commercially viable process for the direct, one-step oxidation of benzene to phenol (equation 3) would not only be simpler than dominant routes now practiced, but would also enable phenol or its derivatives to be marketed unencumbered by the need to find outlets for acetone or carbon dioxide coproducts and, furthermore, would consume no propene.

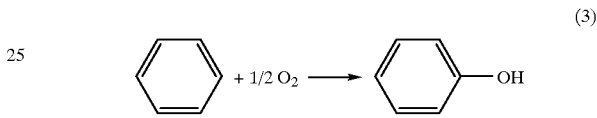

(3)

A number of workers have produced phenol from benzene over the years using molecular oxygen (or air) as the oxidant over a variety of catalysts, usually at high temperature. Unfortunately, ineluctable deep oxidations of benzene generally occur at the needed temperatures which lead to ring cleavage products such as carbon dioxide, carboxylic acids or anhydrides such as maleic anhydride, in toto resulting in poor selectivity from hydroxylation.

More selective hydroxylation of benzene without ring cleavage can be achieved at reasonable space-time yields using other oxidants such as hydrogen peroxide, nitrous oxide, tert-butyl or cumyl hydroperoxide, but these oxidants are up to 50 times more costly per oxygen equivalent than is dioxygen. In still other catalytic processes, molecular oxygen serves as the oxidant, but a stoichiometric co-reactant such as carbon monoxide or hydrogen must be co-fed to the catalyst. This practice not only augments the process costs to prohibitive levels, but also represents an engineering challenge to overcome heightened possibilities for uncontrolled oxidations or explosions. Certain of these processes are patented or described in publications; see, for example, K.-H. Chao et al., U.S. Pat. Nos. 4,982,015 and 4,992,600; Nemeth et al., U.S. Pat. No. 5,233,097; Kharitinov et al., U.S. Pat. No. 5,110,995; Sasaki et al., Bull.Chem.Soc.Jpn., 2850 (1994); Jintoku et al., Chem.Lett. 1687 (1990); Miyake et al., Appl.Cat. A, 131, 33 (1995); A. Matsudo et al., Jap.Pat. No. J03236338-A (1991).

In contrast, there is no previously known route to produce phenol from benzene which uses molecular oxygen as the sole oxidant with no requirement for a coreductant that yields phenol with sufficient selectivity and at sufficient space-time-yield so as to be commercially viable. The present invention provides such a process using $O_2$ with low severity reaction conditions and good selectivity. An advantage of the present invention is to provide a method for the hydroxylation of aromatic compounds which does not require the added reagent and engineering costs and operational risks associated with the use of coreductants such as hydrogen or carbon monoxide. A further advantage of the present invention is to provide a method for the hydroxylation of aromatics which can use molecular oxygen as the terminal oxidant thereby avoiding the need for more expensive oxidants.

SUMMARY OF THE INVENTION

The present invention comprises a process for catalytic hydroxylation of aromatic hydrocarbons which comprising contacting aromatic feedstock with oxidant comprising molecular oxygen, under suitable reaction conditions, in the presence of a catalyst comprising three essential components: a support; transition metal selected from the group consisting of vanadium, niobium, copper, palladium, nickel and silver, or combinations thereof, and a promoter comprising a multidentate chelating, binucleating ligand. The catalysts may further comprise additional metal ions. The process is particularly suited, for example, to the one-step conversion of benzene to phenol.

DETAILED DESCRIPTION OF THE INVENTION

The present invention comprises a process for catalytic hydroxylation of aromatic hydrocarbons which comprising contacting aromatic feedstock with oxidant comprising molecular oxygen, under suitable reaction conditions, in the presence of a catalyst comprising three essential components: a support; transition metal selected from the group consisting of vanadium, niobium, copper, palladium, nickel and silver, or combinations thereof; and a promoter comprising a multidentate chelating, binucleating ligand. The catalysts may further comprise additional metal ions. No stoichiometric co-reductant is necessary according to the process of the present invention. The process is particularly suited, for example, to the one-step conversion of benzene to phenol.

The Process

The process of the present invention pertains to the hydroxylation of aromatic feedstocks without the introduction of stoichiometric co-reductant to the system; e.g., without $H_2$ added to the $O_2$ oxidant system. This does not exclude the presence of initiators or modifiers of the catalyst which may be present in situ prior to steady-state operations; the presence of such initiators or modifiers is within the scope of the present invention.

Under some reaction conditions that are suitable for the ring hydroxylation to occur, side chain oxidation may also occur competitively. Side chain oxidation would consume a portion of the oxidant in the reactor; nevertheless, such reactions are within the scope of the present invention, provided that ring hydroxylation also takes place. More usually, one would prefer to minimize selectivity for side chain oxidation, and in such case, process conditions and/or catalyst components could be selected to mitigate the degree of side chain oxidations.

The process can be conducted over a range of reaction temperatures and pressures. The temperature may be in the range from 70 to 400° C.; preferably 150 to 280° C.; and more preferably 180 to 240° C. The pressure may be in the range from 0 to 6000 psig; preferably 100 to 2000 psig; and more preferably 300 to 900 psig. Preferably, the reaction is carried out under conditions outside the explosive range for the temperature, pressure and oxygen concentrations employed.

Suitable oxygen concentrations would comprise from 1 to 95 volume percent (vol. %) of oxygen in the gas phase at the temperature and pressure of the reaction; preferably the oxygen concentration is 5 to 50 vol. %; more preferably, 7 to 15 vol. %. To avoid explosive concentrations of oxygen, particularly in a continuous reactor, it may be desirable to pre-mix oxygen or air and steam to dilute the oxygen prior to addition of the aromatic feedstock. Suitable weight ratios of aromatic feedstock to water in the reaction process are 2000:1 to 0.2:1; preferably 1700:1 to 50:1; more preferably 1600:1 to 100:1. The oxidant may be molecular oxygen or air or other mixtures comprising $O_2$. Other oxidants, such as hydrogen peroxide, nitrous oxide and organic hydroperoxides, may also be used in the process of the present invention when carried out in liquid phase and under narrower process conditions.

The process can be conducted in different reactor configurations with either liquid phase, vapor phase, multiple liquid phase, or mixed liquid and gaseous phases of the aromatic feedstock depending on the operating parameters. Likewise, a variety of reactor types could be employed to advantage, the focus of the invention being primarily in the use of the catalysts described herein within the temperature, pressure, and oxygen concentration ranges specified herein. Suitable reactor types include, but are not limited to, packed beds, fluidized beds, slurry phase reactors, stirred tank reactors, and reactive distillation columns. Preferably, an isothermal reactor is used to carry out the process of the invention.

The Feedstocks

The aromatic feedstocks suitable for use in the process of the invention comprise unsubstituted aromatics, such as benzene and naphthalene, and compounds in which the aromatic nucleus is substituted with one or more substituents. Suitable substituted aromatic compounds may comprise aromatics substituted with one or more of the following substituents: lower alkyl groups such as methyl, ethyl, propyl, butyl; lower alkoxy groups such as methoxy, ethoxy, propoxy, etc.; halogen atoms such as chlorine, bromine, fluorine, iodine; amino and alkylamino groups; carboxyl, nitro, nitroso, sulfo, sulfone, sulfoxy groups. The foregoing list is not intended to be exhaustive and other substituents, alone or in combination with each other and/or the foregoing, may be incorporated into the feedstock ring systems so long as such substituents do not prevent ring oxidation.

The Catalysts

The catalysts useful in the process of the present invention consist of three essential components: a support system capable of dispersing metal complexes; at least one transition metal ion (or mixtures of several metal ions) chosen from the group consisting of vanadium, niobium, copper, palladium, nickel and silver and combinations thereof; and an organic promoter chosen from the classes of compounds described below. The organic promoter may or may not be a ligand to the metal ions, i.e., the metals ions may or may not be complexed to the promoter ligand. Additional organic or inorganic ligands in addition to the particular promoter compounds of this invention may or may not be present. Metal ion components in addition to those chosen from the set of essential metal ions also may be present. There is no general restriction on the method of forming the catalysts, but preferred procedures and embodiments are described below.

Catalyst supports suitable for the catalyst of the present invention preferably permit reasonable dispersion of the metal ion chosen from the set of essential metal ions, or dispersion of those of its complexes that contain the promoter as a ligand, to be maintained during use. Suitable supports may comprise pure metal oxides, mixtures of metal oxides, or doped metal oxides of reasonable stability and inertness under the oxidative reaction conditions utilized in this invention. The metal oxide support may be comprised of molecular sieves, zeolites, or clays, including, for example, intercalated clays and pillared clays. Titanium framework-substituted or vanadium framework-substituted molecular sieves such as TS-1 or [V]-MCM-41, or the like, can be support components, but these are not preferred. Pore structure modifications and surface treatments can be incorporated into the support system before or after incorporation of the essential metal and promoter species upon the support.

Binders and forming agents can be added to the support composites. The supports can exist in a variety of shapes and particle sizes depending on the reactor configuration to be employed and can be formed by extrusion, spray drying, tabletting, sol-gel techniques, etc. with no restriction. Supports can be shaped bodies such as monoliths, rolled corrugated sheets, cylinders, star-shaped extrudates, or more complex shapes. Burn out agents and porosity modifiers can be added and subsequently removed by calcination. The use of all of these techniques and others within the scope of the invention are within the ability of the practitioner of ordinary skill in the art.

In a preferred embodiment of the invention, at least a portion of the catalyst support comprises titanium, vanadium, magnesium, or aluminum species as a bulk component or as a surface-localized component. In a preferred embodiment of the invention, the supports comprise relatively high surface area anatase titanias of greater than 30 $m^2/g$ or comprise high surface area oxides, such as aluminas of greater than 100 $m^2/g$, which have been treated with titanium- or vanadium-containing surface-active agents such that a well-dispersed overlayer containing titanium or vanadium is formed prior to the catalyst preparation step in which the metal ion component chosen from the set of essential metal ions is added. Methodology for preparing titanium oxide overlayers of this type is described in N. S. de Resende et al., *Preparation of Catalysts IV in Scientific Bases for the Preparation of Heterogeneous Catalysts* G. Poncelet et al. (Eds.), Elsevier Science B.V., (1995), pp. 1059 ff., the disclosure of which is hereby incorporated by reference herein.

The essential metal ion components of the catalyst are selected from the group consisting of vanadium, niobium, copper, palladium, nickel, and silver ions, or combinations thereof These essential metals may be present as metal ions or related complex ions. In addition to the "essential metal ions", the catalysts useful in the present invention may further comprise additional metal ions or combinations thereof, particularly transition metals, including the Lanthanide metals; more particularly, metal ions such as cobalt (II), iron(II), iron(III), manganese, titanium (IV), ruthenium, molybdenum, tungsten, tantalum, gadolinium and combinations thereof.

The ratios of essential metal ion to additonal metal ion, and of essential metal ion to promoter can vary over a wide range, but preferred ranges are set forth below. Acceptable loading ranges of metal species, expressed as weight percent loading of total essential metal on a moisture-free basis on the finished solid catalyst, are in the range from 0.1 to 60 weight percent; preferably the range is from 0.5 to 10 weight percent; more preferably the range is from 1.5 to 4.5 weight percent. Molar ratios for total essential metal component (summing over all the elements of essential metal components added) to promoter compound may be in the range from about 0.1 to about 20; preferably, in the range from about 0.5 to 4; and more preferably in the range from about 0.9 to 2.5.

Metal complexes which incorporate the promoter compounds (or derivatives of promoter compounds such as deprotonated versions) as ligands may be preformed and later incorporated on a support; alternatively, the metal ions and promoter compounds can be separately added to a support. Metal ion species chosen from the set of the essential ions or non-essential additional metal ions may have an oxygen-containing species such as oxide, peroxide, superoxide, oxo, hydroxide, or water bonded to them or proximal to them in a molecular lattice structure or unit cell.

The third component of the catalysts useful in the present invention is the organic promoter which comprises a hexa-, octa- or decadentate chelating, binucleating ligand comprising heteroatom sites, and comprising at least one amido or imino group. Ligands with these components may further comprise additional features as set forth below.

Although the promoter may or may not be bonded to metal ions in the active catalyst, the structure of the organic promoter must meet certain requirements related to its ability to bond metal ions. Promoters of this invention are compounds whose fully or partially deprotonated forms can serve as a hexadentate, octadentate, or decadentate chelating, binucleating ligand for two similar or different transition metal ions chosen from the list of essential metal ions, such that each metal ion may be bonded to three, four, or five heteroatom sites of the ligand. Preferably, the promoter is structured such that there can be five-coordinate binding by each metal atom; i.e., each metal binds to five heteroatom sites of the ligand.

The heteroatom sites may be nitrogen, oxygen, sulfur, phosphorus, or arsenic atoms as further described below. The ligand further comprises at least one amido or one imino functionality; in a preferred embodiment, the ligand comprises four symmetrically distributed amido groups (e.g., tetraoxo tetraaza). The binucleating ligand can be acyclic or cyclic, but cyclic structures are preferred.

In preferred embodiments, the metal binding sites which fall between, and separate, the chelated metal ions are preferably bridging sites which can bind both metals in the binucleated system. Preferably, the bridging sites are chosen from hydroxyl, oxy, oxo, or thiol functionalities. Alternatively, the binding sites which fall between, and separate, the metal ions may comprise groups that bind only one metal, such as amino or pyridino sites, but such groups are not preferred in these positions. Binding the metal ions is accompanied by loss of amide, hydroxyl or thiolic protons. As a result, dipositive metal ions, for example, form neutral complexes when bound to the preferred tetraamido-type ligands.

In one set of preferred embodiments, the ligand structure contains additional electron donating substituents beyond the one required amido or imino group. This may be in the form, for example, of multiple amido groups (e.g., tetraamido), or other suitable electron donating groups.

In other preferred embodiments of the promoter, it is preferable to avoid the presence of tertiary hydrogen atoms; however, they may be present in the promoters useful in the present invention.

In certain embodiments, the ligand may be partially or fully fluorinated or otherwise halogenated to impart oxidative stability to the structure. When present, such halogen atoms are preferably substituted for hydrogen atoms on the spacer groups, though they may be present on other sites as well.

The ligand structures may be cyclic or acyclic, chiral or achiral, and symmetric or asymmetric. While the promoters useful in the catalysts of the present invention are not limited by requirements regarding flexibility or topology, it is understood that cavity size, spacer group size and flexibility is such that, preferably, two metal ions, optionally of different atom types and/or different oxidation states, can be accommodated in such a way so as to allow for oxygen binding by the oxidant to one or both metal ions (e.g., superoxo or $\mu$-peroxo binding).

It is understood that some or all of the additional features described herein may be present in various promoters used in forming the catalysts. The promoter has been described herein as a ligand bound to metal ions. However, as noted above, the promoter may or may not be bound to the metals when comprising part of the overall catalyst used in the process of the invention.

An example of a suitable compound for use as a promoter is the 26-membered octaaza macrocycle: 3, 6, 9, 17, 20, 23, 29, 30-octaazatricyclo[23.3.1.1.$^{11,15}$]triaconta-1(29), 11, 13, 15(30), 25, 27-hexaene-2, 10, 16, 24-tetraone, abbreviated TOBP, the structural formula for which is shown below (Figure 1), and which was first described in M. Kodama, T. Koike, and E. Kimura, *Bull. Chem. Soc. Japan* (1995) 68, 1627, which disclosure is hereby incorporated by reference herein.

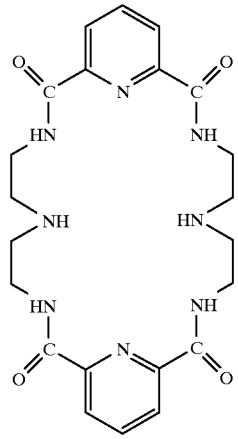

Fig. 1

Several previously unknown metal complexes of TOBP were prepared in our laboratories. Some of these have utility as catalysts for aromatic hydroxylation once supported and used in the manner of this invention. An example of such complexes is [Co(I), Pd(II) (TOBP)]. This product was characterized by NMR, IR electrochemically, by TLC, and by positive ion FAB-MS which showed the major peak at m/z=630 (assigned to M+1).

Another compound which is suitable for use as a promoter is the PROPALD ligand with a structure as generally shown below. For example, the complex [VO(2+), Co(2+)(propald)(OAc)(H$_2$O)$_2$]$^+$, the structure of which is shown below (Figure 2), was prepared. The positive ion FAB-MS showed the highest mass peak at m/z=587 (assigned to M+2).

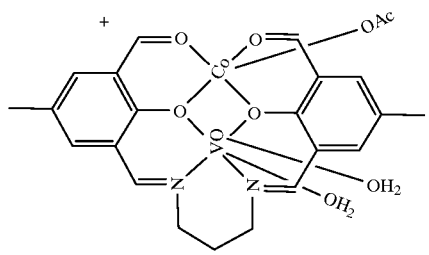

FIG. 2

Many other binuclear complexes with ligands fitting the definition of promoters of this invention were prepared and characterized as described below. For example, another suitable promoter structure, which is a novel composition of matter, is designated EBPA. This structure features larger spacer groups than TOBP which results in increased flexibility to accommodate different size metal ions, each in 4-coordinate fashion. EBPA has the structure shown below (Figure 3).

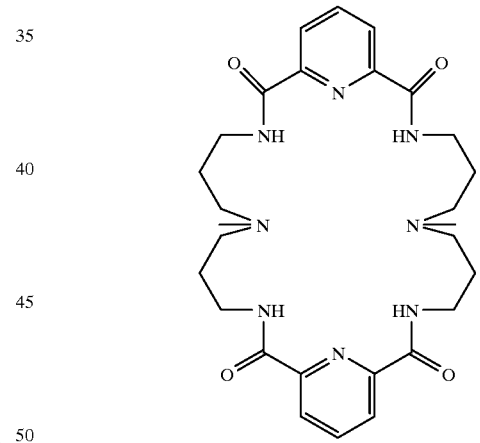

FIG. 3

Another compound useful as a promoter in the catalysts of the present invention is designated IATD and shown below (Figure 4).

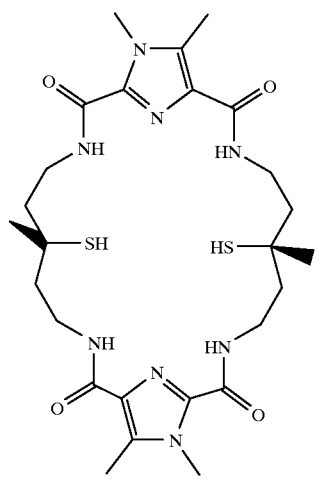

FIG. 4

According to the structure of IATD, thiol groups and amido groups can lose hydrogens when binding metal ions; also, thiolic sulfur atoms act as bridging atoms each capable of simultaneously binding two metals. Electron donating methyl substituents on each thiol-bound carbon atom replace tertiary hydrogen atoms present in the EBPA ligand.

Yet another suitable promoter structure is designated TANSIC and is drawn below (Figure 5):

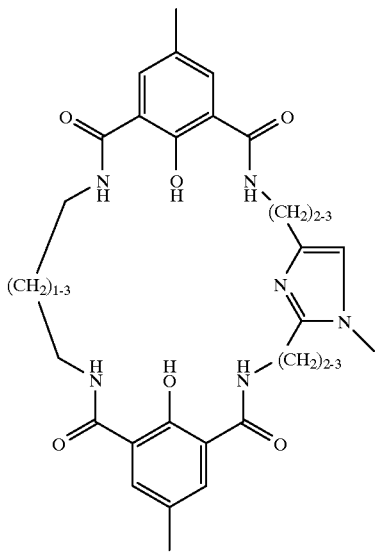

FIG. 5

This structure is non symmetrical and features the capability of losing up to 6 protons to form neutral compounds with two tripositive metal ions or with a dipositive and tetrapositive metal ion. One metal could exist as a 4-coordinate complex and the other as a 5-coordinate complex with deprotonated forms of this ligand. Several variants of this structure are possible. For example, without limiting the scope TANSIC structures suitable for use in the present invention, there may be varying numbers of methylene spacer groups, varying number and types of substituents on the phenolic and/or imidazolic rings, and varying degrees of halogenation of the alkyl spacer groups. Protonated forms of the TANSIC structure are also useful as promoters.

The binuclear ligand designated CYPHIC also meets the criteria for a promoter for the purposes of the present invention. The structure of this ligand as complexed in the form of [Cu, $VO^{2+}$(CYPHIC)(OAc)($H_2O$)$_2$] is shown in Figure 6 below. During the synthesis of this complex, the protonated ligand $H_2$CYPHIC was not isolated.

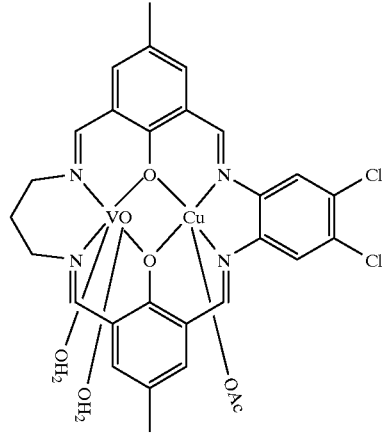

FIG. 6

Catalyst Preparation

Catalysts may be prepared by synthesis of metal complexes comprising the promoter compounds as ligands bound to the metal(s), followed by their incorporation onto the surface of an appropriate support within prescribed loading ranges, followed by drying. Alternatively, the catalysts may be prepared by separately incorporating metal ions and organic promoter compounds onto suitable supports in two or more independent steps. Since some of the preformed complexes are insoluble in common laboratory solvents, when using incipient wetness loading techniques, for example, separate impregnation of each of a metal salt solution and of an organic promoter solution can be a preferred preparative method. Addition of the promoter compound to the support followed by addition of the essential metal component is a generally preferred order of addition, though not essential.

A stoichiometric amount of a base may optionally be added in some cases to enhance deprotonation of the promoter compounds such that metal ions may more readily bind; however, care must be taken to ensure that base addition will not prematurely precipitate metal salts. In some cases, the promoter species cannot be isolated as a discrete compound that is not bound to a metal. It is understood that multiple metals and multiple organic promoters can be added onto the same support particles or shaped bodies within the scope of this invention. Other compounds in addition to promoter compounds may optionally be added to serve as additional ligands or modifiers.

EXAMPLES

The following examples illustrate preparation of catalyst or catalyst components:

Example 1

A sample of the catalyst $VO^{2+}$/TOBP/$TiO_2$ was prepared as follows. A sample of titania (anatase titania) [14.16 g] that had been ground and sieved to 18/35 mesh was warmed in air on a hot plate to about 90° C. TOBP [0.54 g] was dissolved into ethanol and impregnated onto the titania with mixing of the solid; additional ethanol was added to bring the solid to incipient wetness. The solid was dried on a hot plate while exposed to air. An aqueous solution of $VOSO_4.3H_2O$ [0.78 g] was prepared and the solid impregnated with it, followed by drying. A second solution of TOBP [0.26 g] in ethanol was prepared and the solid impregnated with it and air dried. The sample was then dried in a vacuum oven at about 190° C. under full vacuum for 3 hours. This solid, containing a nominal 1.2 wt. % V, was used as a catalyst with no further treatment.

Example 2

A second sample of TOBP-containing catalyst was prepared as above except only one dose of TOBP was added, and the sample washed with water followed by ethanol after impregnation to remove unreacted TOBP, vanadium salts, and sulfuric acid byproduct. The sample was dried as above prior to use.

Example 3

A third catalyst was prepared as follows: A sample of $[Cu^I(VO^{2+})(CYPHIC)(OAc)(H_2O)_2]$ which had been previously synthesized and characterized was dissolved in acetonitrile/ethanol, and the solution impregnated at room temperature onto 18/35 mesh anatase titania that had been previously dried at 130° C. to give a nominal loading of 4 wt. % complex. Acetonitrile was evaporated by stirring the sample with a spatula in a Petri dish on a hot plate in a fume hood. The sample was then placed in a vacuum oven while still moist and heated to about 140° C. under vacuum for about 2 hours.

Example 4

A fourth catalyst sample, $Cu^+$/TOBP/SK-500 zeolite, was prepared as follows: 14.07 g of a commercial sample of 1/16 inch extrudates of SK-500 zeolite were boiled repeatedly in distilled water following by decanting to remove soluble sodium silicate impurities. Copper(I)acetate [2.49 g] was dissolved into ca. 80 mL of dilute acetic acid with stirring and heating to give a blue solution. The copper solution was added to the washed zeolite and the mixture boiled for 10 minutes. After decanting, the solid was washed four times with boiling distilled, deionized water and hot acetonitrile. TOBP [0.13 g] solid was sprinkled over the solid zeolite and the mass just covered with ethanol. After thoroughly mixing with a spatula while heating on a hot plate, the solid was washed with additional ethanol and acetonitrile to remove unreacted TOBP. The sample was dried in a Petri dish on a hot plate, followed by further drying at 165° C. in a vacuum oven for 1 hour.

Example 5

The promoter ligand EBPA was synthesized for the first time by the following method. An ethanolic solution (400 mL) of dimethyl-2,6-pyridinecarboxylate [20 mmol, 3.9 g] and dipropylenetriamine [20 mmol, redistilled] was prepared and allowed to reflux for 4 days. After the reflux period, the solvent was evaporated to give an amber oil. Redissolution in ethanol or trichloromethane, followed by cooling in a refrigerator, failed to produced a precipitate. Extraction of the oil with water at room temperature, followed by rotary evaporation of the separated water layer, produced 3.1 g of an amber solid [12.5% yield prior to purification]. The solid showed a clean m/z=553 signal in the FAB positive ion mass spectrum and a single component besides the original spot in normal phase TLC using $CHCl_3$, as the mobile phase with a Rf of 0.21. An attempt to recrystallize the solid from hot ethanol failed to produce crystals; hence, the solid was used without further purification in subsequent tests.

Example 6

The promoter $H_2PROPALD$, as a free ligand (1,3-diaminopropane-4-methyl-2,6-diformylphenol), was synthesized as follows. 2,6 diformylcresol [14.3 mmol, 2.34 g] was dissolved in dry ethanol and allowed to condense with propylenediamine [7.15 mmol, 0.53 g, redistilled] under reflux conditions. Mass spectroscopy showed the major peak to be m/e=366 and a smaller peak at m/e=338; Proton NMR (CDCl3) indicated peaks at 14.24, 10.44, 8.36, 7.43, 7.27, 3.74, 2.27, and 2.12 ppm.

Example 7

The CYPHIC promoter [Co(II),Cu(I)(cyphic)](OAc), as mixed isomers, was synthesized as follows. Dihydrogen PROPALD [4.3 mmol, 1.576 g] was dissolved into methanol. Cobalt(II) acetate [4.3 mmol, 1.07 g] and copper(I) acetate [4.3 mmol, 0.527 g] were dissolved into another aliquot of methanol. The methanol solutions were combined and stirred for 4 hours, then 4,5-dichlorophenylenediamine [4.3 mmol, 0.761 g] added to the solution with vigorous stirring. The resulting solution was refluxed overnight then cooled and evaporated to dryness. The solid was recrystallized from hot water. FAB-MS indicated the major m/e peak to be 628 (M+2 of [Co(II),Cu(I)(cyphic)]+, rel intensity= 100%); 626 (90%); 630 (37%) and indicated small impurity peaks at 633 and 780 from which it was estimated that impurity level was about 12%.

Example 8

The promoter [Cu,Co(cyphic)](OAc), as a single positional isomer, was synthesized as follows. Preformed and isolated [Cu(propald)] complex [0.6 mmol, 0.257 g] was combined with cobalt (II) acetate [0.6 mmol, 0. 149 g] and stirred for 1 hour at room temperature in methanol. Dichlorophenylenediamine [0.6 mmol, 0.106 g] was added and the solution refluxed overnight. Upon cooling in a refrigerator, 330 mg of a solid were isolated. FAB-MS (positive ion) indicated that the proper compound had been prepared; No quantitative analysis was performed to determine the isomer purity, but TLC in $CH_2Cl_2$ showed only one spot on silica-gel plates.

Example 9

The promoter [Co(II),Pd(II)(TOBP)] was synthesized as follows. $H_4TOBP$ free ligand [1 mmol, 0.47 g] was dissolved in ethanol and an ethanolic solution of cobalt acetate added [1 mmol, 0.25 g]. The solution was stirred 1 hour, then palladium acetate added [0.224, 1 mmol] which had been predissolved in a minimum of ethanol. The ethanol volume was brought up to 250 mL and the solution refluxed with stirring for 2 hours. An initially formed precipitate was filtered off, and the supernatant solution evaporated to dryness yielding the desired product. FAB-MS (positive ion) indicated a clean major peak at m/e=630 (M+1), [No peak at 469 was evident (M+1 of $H_4TOBP$)]; FTIR analysis indicated the CO stretch to have moved from 1669 cm-1 in free $H_4TOBP$ to 1596 cm-1 in the heterobinuclear complex.

Example 10

The synthesis of promoter IATD may be carried out in a manner similar to that described for EBPA using the precursors, dimethyl-1-methyl-2,4-imidazoledicarboxylate and 3-methyl-3-mercapto-pentane-1,5-diamine, which in turn may be prepared by standard synthetic methods. Modifications to the procedure involve the use of appropriate protecting groups to prevent the destruction of sensitive functional groups.

The following examples illustrate use of the catalysts for the oxidation of benzene:

Examples 11–22

A number of catalysts were prepared and tested in several types of reactors. These tests showed positive results for selectivity for ring-hydroxylation products and for the space-time yield of phenol when using benzene as a feedstock. A set of standard conditions, as shown in Table I, were chosen to screen catalysts in a particular reactor system configured around a gold-plated CSTR reactor fitted with Robinson-Mahoney internals to hold solid catalyst (RM-CSTR).

as opposed to stoichiometric reaction, has taken place. Selectivity is much higher for the TOBP-treated catalyst also.

Comparison of Run 11 with Run 12 shows the effect of vanadium loading. Comparison of Runs 12, 15 and 16 shows the effect of different supports including a titanium framework-substituted zeolite, TS-1, in Run 16.

Run 18 is a catalyst prepared with a mononuclear vanadium porphyrin complex with electron-withdrawing substituents on a preferred support showing that this type of catalyst is less effective than the catalyst of Run 12 based on a binuclear ligand-type promoter, TOBP. Product analysis indicated that this ligand decomposed under reaction conditions. Runs 19 and 22 show that other kinds of vanadium compounds which are competent oxidation catalysts in other applications are not effective in this application as

TABLE I

Benzene Oxidation over Selected Catalysts in RM-CSTR[a]

| Run | 11 | 12 | 13 | 14 | 15 | 16 | 17 | 18 | 19 | 20 | 21 | 22 |
|---|---|---|---|---|---|---|---|---|---|---|---|---|
| CATALYST | V(IV)/ TOBP/ TiO$_2$ | V(IV)/ TOBP/ TiO$_2$ | V(IV)/ TOBP/ TiO$_2$[b] | V(IV)/ TiO$_2$ (no prom) | V(IV)/ TiO$_2$ Na—Y | VOSO$_4$/ TS-1 | VO(pro paid)/ TiO$_2$ | VO(C$_3$F$_2$)$_4$ Ph$_2$P/ TiO$_2$ | VPO (2 types) | Cu(1)/ TOBP/ Na—Y | Cu(1)/ TOBP/ Na—Y | H$_4$PV Mo$_{11}$O$_{40}$ SiO$_2$ |
| ACTIVE METAL | V | V | V | V | V | V | V | V | V | Cu | Cu | V,Mo |
| WT % ACT MET | 0.5 | 1.2 | 1.2 | 1.2 | 0.9 | 2 | 0.26 | 2.5 | | 2–3 | 2–3 | |
| T(°C.) | 180 | 180 | 180 | 180 | 180 | 180 | 181 | 180 | 180–225 | 180 | 225 | 180 |
| P (psig) | 827 | | | 840 | 840 | 827 | 840 | 849 | 840 | 840 | 1,200 | 840 |
| MOL % CONV OF BENZENE | 1 | 1 | 0.4 | LOW | 0.2 | 0.4 | 0.5 | 0.2 | ~0 | 0.5 | 1 | 0.06 |
| % C SELECT. TO PhOH | 41 | 87 | 43 | | 79 | 12 | 77 | | 41 TRACE | 81 | 40 | 5 |
| % SEL TO ArOH | 43 | 94 | 2% to aniline[b] | | | 23 | 79 | | | | | |
| TRNOVRS | | 6 | 6 | | 23/ (VO) [64 tot[c]] | | 4.5 | 0.08 | | | | |
| STY-3h | 5.4 | 14.1 | | 1.8 | 3.4 | 0.9 | 6.1 | 1.3 | | 11.5 | | <1.5 |
| STY-1h | 14.2 | | | | | | | | | | | |

[a]Measurements after 3 hours on-stream in semi-batch mode RM-CSTR reactor; feed benzene saturated with water unless noted otherwise; T = 180+/−3°; P = 840 +/− 5 psig; 7% O$_2$(by vol) under reaction conditions.
[b]NH3 added to feed in this run.
[c]Restarted over several days with fresh benzene added each day.
[d]mmoles aromatic hydroxyls/mmoles (VO)$_2$; does not count CO$_2$, biphenyl, etc.

This reactor was operated isothermally in semi-batch mode: continuous in gaseous oxygen plus nitrogen and batch in water and benzene which were condensed back into the reactor. Analysis of both gaseous and collected liquid product aliquots was done off-line in several steps by using gas chromatographic and Gc-MS methods calibrated against known concentrations of authentic samples of reaction products. A 10 mL bed downflow isothermal packed bed continuous reactor was also used to evaluate catalysts and process conditions.

Table I shows the results of some comparative testing of selected samples of catalysts. Comparison of Run 12 with Run 14 of Table I demonstrates the effect of adding the TOBP promoter to the catalyst on the preferred support: space-time yield at 3 hours on-stream improves from 1.8 to 14.1 upon incorporation of TOBP promoter into the catalyst and the number of turnovers in Run 12 proves that catalysis, catalysts. These findings further indicate the uniqueness of the catalyst system of the present invention.

Run 20 compared to Run 21 shows the effect of changing temperature and pressure using a copper-based catalyst. As temperature is raised from 180° C. to 225° C. and pressure is raised from 840 psig to 1200 psig, selectivity to phenol is halved and conversion is doubled.

Comparison of Run 12 with Run 17 shows a comparison between: 1) a catalyst made using TOBP, a cyclic amido ligand type used as a promoter, by step-wise impregnation of promoter then enough vanadium to result in 1.2% vanadium in the final catalyst, and 2) a catalyst prepared by preforming a complex with an acyclic potentially binucleating ligand with imine groups instead of amido groups, then depositing the preformed complex onto a support to give a final loading of 0.26% vanadium. The TOBP catalyst shows better results; but it is noted that the latter catalyst shows remarkable results given the low loading of vanadium.

What is claimed is:

1. A process for catalytic ring hydroxylation of aromatic hydrocarbons comprising contacting aromatic feedstock with oxidant comprising molecular oxygen under suitable reaction conditions in the presence of a catalyst comprising:
   (a) a support;
   (b) transition metal selected from the group consisting of vanadium, niobium, copper, palladium, nickel and silver, or combinations thereof; and
   (c) a promoter comprising a multidentate chelating, binucleating ligand (i) comprising heteroatom sites comprising nitrogen, oxygen, sulfur, phosphorus or arsenic atoms or combinations thereof, and (ii) comprising at least one amido or imino group.

2. The process of claim 1 wherein said support is selected from a group consisting of metal oxides, molecular sieves, zeolites and clays.

3. The process of claim 2 wherein said metal oxides are selected from the group consisting of pure metal oxides, mixed metal oxides and doped metal oxides.

4. The process of claim 2 wherein said molecular sieves are selected from the group consisting of titanium framework-substituted and vanadium framework-substituted molecular sieves.

5. The process of claim 2 wherein said clays are selected from the group consisting of intercalated clays and pillared clays.

6. The process of claim 2 wherein said support comprises compounds comprising titanium, vanadium, magnesium or aluminum or combinations thereof.

7. The process of claim 6 wherein said support comprises titania.

8. The process of claim 1 wherein said catalyst further comprises ions of one or more additional metals.

9. The process of claim 8 wherein said additional metals comprise transition metals.

10. The process of claim 9 wherein said additional metals comprise cobalt, iron, manganese, titanium, ruthenium, molybdenum, tungsten, tantalum or gadolinium or combinations thereof.

11. The process of claim 1 wherein said ligand is capable of binding two atoms of said transition metal to three to five heteroatom sites of said ligand.

12. The process of claim 11 wherein said ligand is capable of binding said atoms of transition metal to five heteroatom sites of said ligand.

13. The process of claim 1 wherein said ligand comprises four symmetrical amido groups.

14. The process of claim 1 wherein said ligand comprises TOBP, PROPALD, EBPA, IATD, TANSIC or CYPHIC, or metal coordinating complexes thereof.

15. The process of claim 1 wherein said catalyst comprises more than one promoter.

16. The process of claim 1 wherein said reaction conditions comprise a temperature in a range from 70 to 400° C. and a pressure in a range from 0 to 6000 psig.

17. The process of claim 16 wherein said temperature is in a range from 150 to 280° C.

18. The process of claim 17 wherein said temperature is in a range from 180 to 240° C.

19. The process of claim 16 wherein said pressure is in a range from 100 to 2000 psig.

20. The process of claim 19 wherein said pressure is in a range from 300 to 900 psig.

21. The process of claim 1 wherein said aromatic feedstock comprises unsubstituted or substituted aromatic compounds.

22. The process of claim 21 wherein said aromatic feedstock comprises benzene or naphthalene.

23. The process of claim 22 wherein said aromatic feedstock comprises benzene.

24. The process of claim 21 wherein said aromatic feedstock comprises substituted aromatic compounds comprising one or more substituents comprising alkyl groups, alkoxy groups, halogen atoms, amino groups, alkylamino groups, carboxyl groups, nitro groups, nitroso groups, sulfo groups, sulfone groups, or sulfoxy groups or combinations thereof.

* * * * *

UNITED STATES PATENT AND TRADEMARK OFFICE
CERTIFICATE OF CORRECTION

PATENT NO. : 5,952,532

DATED : 9/14/99

INVENTOR(S) : Durante et al.

It is certified that error appears in the above-identified patent and that said Letters Patent is hereby corrected as shown below:

Columns 13 and 14, In Table 1, under Run 17 delete "paid" and insert -- pald -- therefor.

Columns 13 and 14, In Table 1, under Run 22 insert -- / -- between "$Mo_{11}O_{40}$" and "$SiO_2$".

Column 13, Line 56, delete "Gc-MS" and insert -- GC-MS -- therefor.

Signed and Sealed this

Twenty-third Day of May, 2000

Attest:

Q. TODD DICKINSON

*Attesting Officer*  *Director of Patents and Trademarks*